United States Patent [19]
Bruzzese

[11] Patent Number: 5,914,321
[45] Date of Patent: Jun. 22, 1999

[54] ANTITUMORAL METHOD BY ADMINISTRATION OF PARTRICIN DERIVATIVES

[75] Inventor: Tiberio Bruzzese, Milan, Italy

[73] Assignee: Prospa B.V., He Hoofddorp, Netherlands

[21] Appl. No.: 08/953,751

[22] Filed: Oct. 17, 1997

[30] Foreign Application Priority Data

Sep. 19, 1997 [IT] Italy .................................. MI97A2138

[51] Int. Cl.⁶ .................................................... A61K 31/70
[52] U.S. Cl. ................................................................ 514/31
[58] Field of Search ................................................. 514/31

[56] References Cited

U.S. PATENT DOCUMENTS 5,298,495    3/1994    Bruzzese et al. ......................... 514/31

Primary Examiner—Jerome D. Goldberg
Attorney, Agent, or Firm—Oblon, Spivak, McClelland, Maier & Neustadt, P.C.

[57] ABSTRACT

The use of some semisynthetic derivatives of the antifungal polyene partricin to selectively hinder the growth of tumor cells is here described.

Their use can be associated with the use of other known antineoplastic agents, in particular in the cases where a resistance to these agents is present or has developed.

The invention can be applied to systems of cell cultures as well as to the therapeutic practice.

13 Claims, 2 Drawing Sheets

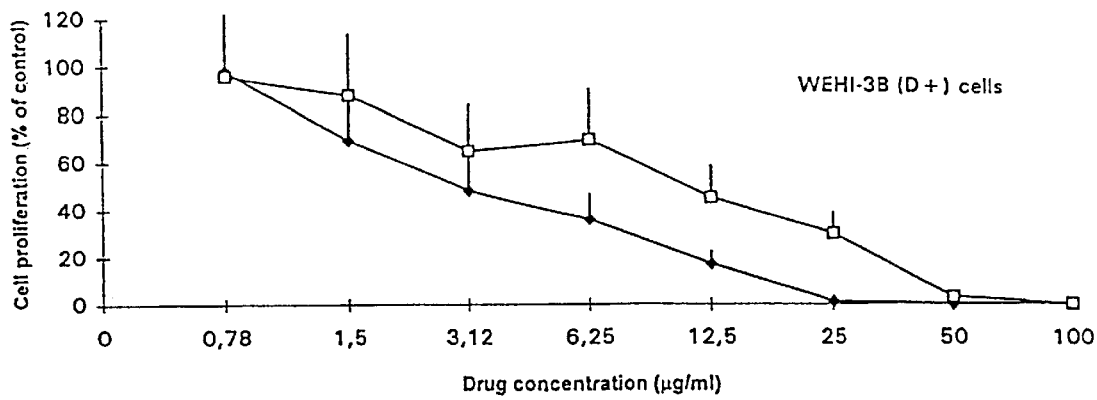
Figure 1 - Dose-response curve of the cytotoxic effect on *in vitro* cell proliferation (MTT test).
(♦) SPA-S-843    (□) Amphotericin B
Each point is the mean ± s.e. of 3 experiments conducted in triplicate.
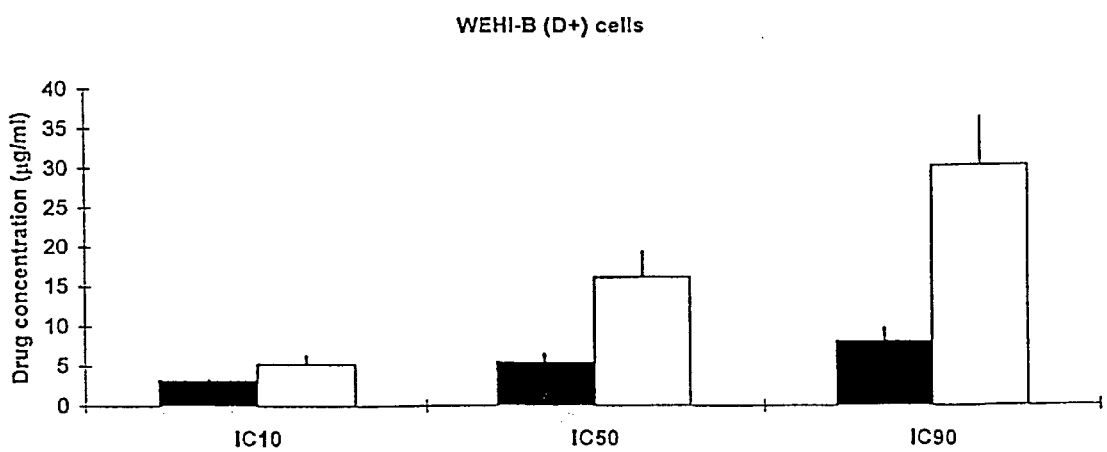
Figure 2 - IC values of SPA-S-843 and amphotericin B assessed in *in vitro* cell proliferation test.
(■) SPA-S-843    (□) Amphotericin B
Each value is the mean of 3 experiments conducted in triplicate.

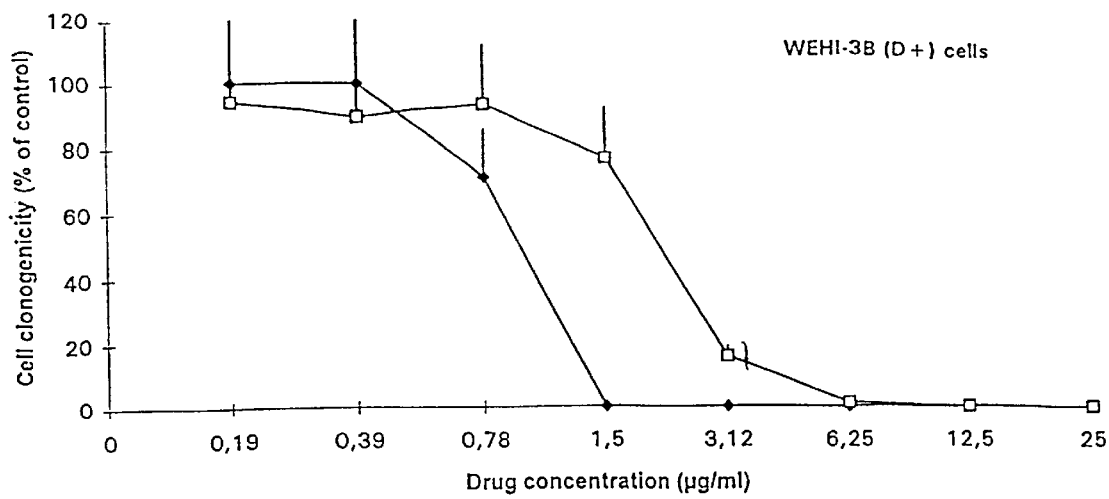
Figure 3 - Dose-response curve of the cytotoxic effect on cell clonogenicity ( agar test).
( ♦ ) SPA-S-843     ( □ ) Amphotericin B
Each point is the mean ± s.e. of 2 experiments conducted in duplicate.
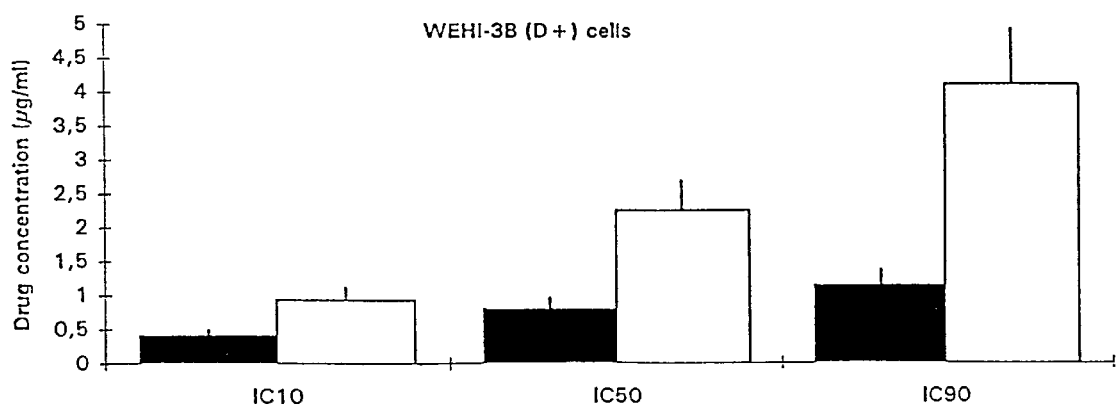
Figure 4 - IC values of SPA-S-843 and amphotericin B assessed in *in vitro* cell clonogenicity test .
(■) SPA-S-843     ( □ ) Amphotericin B
Each value is the mean of 2 experiments conducted in duplicate.

ANTITUMORAL METHOD BY ADMINISTRATION OF PARTRICIN DERIVATIVES

Partricin, a mixture of partricin A and partricin B (The Merck Index XII Ed., no. 7181), is a polyene substance obtained through fermentation of a special S. aureofaciens strain, and exhibiting very high antifungal activity.

Since the substance as such is rather toxic to be used in therapy, several structural modifications were brought to it by semisynthetic route, using partricin itself or its individual constituents as the raw material, specially partricin A. Examples of the afore-said derivatives are given, among others, in European Patent Applications EP-A-0434943 and EP-A-0489308 as well as in U.S. Pat. No. 3,780,173 (see also the Merck Index 12th Ed., 5891) and U.S. Pat. No. 3,961,047. Several of these derivatives were found more active as antifungal agents, and much less toxic, than the starting substances and than the present reference standard in therapeutic practice, that is, amphotericin B.

In the course of experimental investigations, wherein partricin derivatives were tested on cell cultures with a view to preventing their contamination by fungi—which was suggested by the high antifungal activity of these derivatives, coupled with their excellent tolerance by eukaryote cells at the concentrations active against fungi and molds—we have surprisingly found—and it is the subject of the present patent application—that some tumor cell lines were extraordinarily sensitive to such substances; also at very reduced concentrations (but, at any rate generally higher than those carrying out antifungal activity in the respective cell culture), and for a limited exposure time, a total blockage of cell growth was observed, with final complete mortality of the cells.

The classes of partricin derivatives suitable for the use and methods of this invention comprise esters and amides on the carboxyl group, optionally substituted on the primary amino group of the mycosamine radical with acyls.

The derivatives of partricin A and/or B which we have used, are the same as described in European Patent applications EP-A-0434943, EP-A-0489308, U.S. Pat. No. 3,780, 173 and U.S. Pat. No. 3,961,047 are, in practice, esters and amides on the carboxyl group at C-18 of the macrolide ring, optionally substituted on the amino group of the mycosamine radical with an acyl group and their salts with organic and inorganic acids acceptable in the pharmacological and pharmaceutical practice.

In particular, the amide derivatives of partricin A and/or B described in European Patent application EP-A-0434943 (corresponding to U.S. Pat. No. 5,296,597) are secondary and tertiary amides of the carboxyl group at C-18 of the macrolide ring. In partricin A and/or B derivatives described in patent application EP-A-0489308 (corresponding to U.S. Pat. No. 5,298,495), the carboxyl group at C-18 of the macrolide ring forms a $C_1$–$C_6$ alkyl ester or an amide, neutral or containing an additional basic nitrogen containing function, and the primary amino group of the mycosamine portion forms an aminde bond with the carboxyl group of an aliphatic acid of 2–4 carbon atoms containing an additional basic nitrogen containing group.

Other derivatives of partricin suitable for the use and methods of this invention are the alkyl esters of partricin, e.g. $C_1$–$C_4$ alkyl esters, in particular, the methyl ester of partricin complex (mepartricin) and of partricin A and/or B, described in U.S. Pat. No. 3,780,173 and U.S. Pat. No. 3,961,047.

The description and examples of the afore-said European patents, their corresponding U.S. Pat. No. 5,296,597 and U.S. Pat. No. 5,298,495 counterparts, of U.S. Pat. No. 3,780,173 and U.S. Pat. No. 3,961,047 relative to the preparation of partricin A and/or B derivatives mentioned above, are incorporated by reference in the present patent application.

The scope of this invention includes the use of those derivatives of partricin A and/or B having the usual spatial configuration of partricin as well as those derivatives of partricin A and/or B having "all trans" configuration which can be obtained, for instance, by UV or sun light exposure (Bruzzese T. et al, Il Farmaco Ed. Sci. 4, 331–334, 1974).

Derivatives of partricin A and B are compounds represented by formula (I):

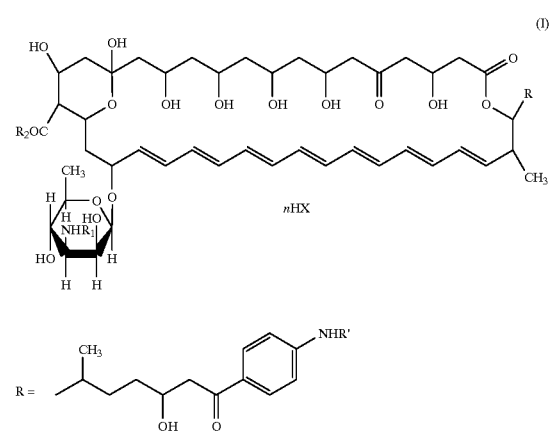

wherein

R' is a hydrogen atom or a methyl group;

$R_1$ is an aminoacyl radical —$CO(CH_2)_m NR_3 R_4$, wherein m=1, 2 or 3, $R_3$ and $R_4$, which can be the same or different, are a hydrogen atom or a $C_1$–$C_3$ alkyl group or form with the nitrogen atom to which they are bound, a five- or six-membered heterocyclic ring optionally containing another hetero atom selected from the group consisting of O, S and N, wherein said N may be substituted by a methyl or 2-hydroxyethyl group;

$R_2$ is a hydroxy, $C_1$–$C_6$ alkoxy, $NR_3 R_4$ amino or —NH—$(CH_2)_m$—$NR_3 R_4$ aminoalkylamino group, wherein m, $R_3$ and $R_4$ are as defined above, or a substituted —NH—$(CH_2)_m$—$R_5$ alkylamino group, wherein m is as defined above, and $R_5$ is a five- or six-membered heterocyclic ring, wherein the heteroatom is nitrogen which may be substituted with a methyl or ethyl group;

X is the anion of a pharmaceutically acceptable organic or inorganic acid; and n is 0, 1 or 2.

The structural group $R_1$ may be selected from the group consisting of:

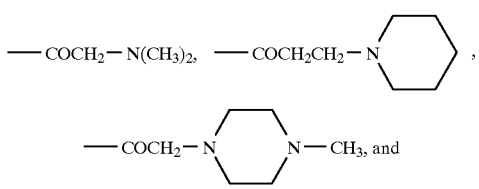

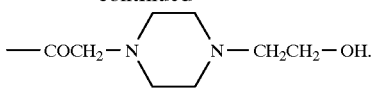

The structural group $R_2$ may be selected from the group consisting of:

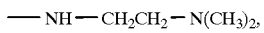

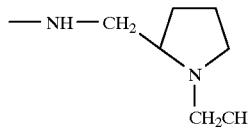

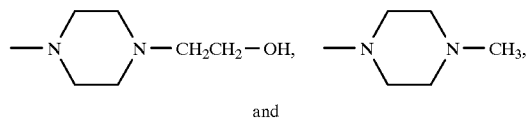

and

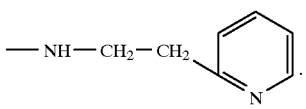

X is the anion of an acid selected from the group consisting of aspartic, glutamic, glycolic, glucuronic, gluconic and ascorbic acid.

One of the compounds found most effective in the course of our study is a partricin A derivative, that is, N-dimethylamino-acetyl-partricin A 2-dimethylaminoethylamide. Following transformation to the corresponding salts, in particular, to diascorbate (laboratory code SPA-S-843), the compound becomes water soluble, unlike many natural polyenes, and can easily be employed in in vitro cultures, as well as easily used in pharmaceutical formulations for the clinical application by parenteral route (injectable ampuls, infusions etc.).

The above reported finding relative to the surprisingly marked toxicity against some tumor cell lines, leads us to foresee the use of these compounds in the clinical practice as antineoplastic drugs, after having tested in vitro cell sensitivity of each tumor line (for example, leukemia, lymphoma, myeloma, melanoma, carcinoma, sarcoma and other tumors).

Their utilisation is also foreseeable in combination with other drugs of better known antineoplastic activity (platinum derivatives, doxorubicin, vincristine, methotrexate, etc.) considering, at any rate, that their interaction (common with the other polyenes) with the membrane sterols, is damaging to cell membrane which favours intracellular penetration and accumulation of the other antineoplastic drugs, leading to synergic effects.

A representative example of SPA-S-843 cell toxicity on murine WEHI-3B (D+) myelomonocytic leukemia cells (Pessina et al., "Susceptibility of leukemia cell lines to quinolones and induction of resistance to ciprofloxacin in WEHI-3B (D+) leukemia cells "Cancer J., 6, 291–7, 1993) is here reported with no limiting intent of the invention.

Substances: SPA-S-843 and amphotericin B were dissolved in sterile bidistilled water to a concentration of 2000 µg/ml. The working solutions were prepared in McCoy medium supplemented with penicillin+streptomycin (100 U/ml+100 µg/ml) at the concentrations of from 200 µg/ml to 1.56 µg/ml by subsequent serial 1:2 dilutions.

The murine WEHI-3B (D+) myelomonocytic leukemia cells were maintained through subcultures in 25-cm² plastic bottles in McCoy medium (Seromed, Germany) containing 5% FCS (Gibco, USA).

Cell sensitivity to the toxic action of SPA-S-843 in comparison with that of amphotericin B, taken as reference substance, was determined by two different methods:

A) Microtiter test (MTT) (Pessina et al. "In vitro short-term and long-term cytotoxicity of fluoroquinones on murine cell line", Ind. J. Exp. Biol., 32, 113–8, 1994).

B) Clonogenic test in agar (Pessina et al. "Inhibition of murine leukemia cell—WEHI-3B and L1210—Proliferation by cholera toxin B subunity", Biochem. Biophys. Acta, 1013, 206–11, 1989).

DESCRIPTION OF TESTS

Cytotoxicity by MTT: it is a microtiter test using 3-(4,5-dimethyl-2-thiazolyl)-2,5-diphenyl-2-H-tetrazolium bromide (MTT—Sigma, USA) according to Mossman T. (J. Immunol. Methods, 65, 55–63, 1983) modified according to Kriegler A. B. et al. (J. Immunol. Methods 103, 93–102, 1987).

In brief, 50 µl of a 1:2 serial dilution from 2 µg/ml to 0.015 µg/ml of each of the two drugs were placed in 96 wells of flat-bottom Microtiter plates then each well was added with a 50 µl cell suspension (6×10³ cells/ml). The cultures were incubated for 7 days at 37° C. in air+5% $CO_2$ and finally 20 µl of MTT at a conc. of 5 mg/ml in PBS were added to each well. After 3-h incubation at 37° C. the cultures were destroyed with 100 µl of a lytic buffer prepared with sodium dodecylsulfate/dimethylforma-mide/acetic acid/HCl. After further overnight incubation, the optical density (OD) at 620 nm was determined with a microplate LP200 detector. The O.D. of the wells with no cells was considered as 0% proliferation. The O.D. of the wells with growing cells in drug-free medium was considered as 100% proliferation. The drug cytotoxicity was calculated as the minimum concentration leading to 50% inhibition of cell growth in vitro ($IC_{50}$).

Cytotoxicity by clonogenic test in agar

The clonogenic capacity of WEHI-3B(D+) cells was tested by culturing 300 cells in 0.3 ml of complete enriched medium [McCoy+10% FCS, 10 mM sodium pyruvate, 4% NEAA (10×), 4% Mem Vit (100×)]+0.3% agar in 35 mm Petri plates.

SPA-S-843 and amphotericin B (100 µl) had previously been added to the Petri plates at serial concentrations of from 25 to 0.19 µg/ml. The control plates contained 100 µl of culture medium. The colonies were counted after 7 days of incubation at 37° C. in an atmosphere of air+5% $CO_2$.

Results

The cytotoxicity of the two drugs on cell proliferation, evaluated with the MTT test, is expressed as % of the O.D. values measured in the controls (untreated cells, O.D. 1133.5±48).

BRIEF DESCRIPTION OF THE DRAWINGS

The diagrams in FIG. 1 report the dose/response curves. As confirmed by linear regression analysis, the toxic effect of SPA-S-843 and of amphotericin B shows a dose-related kinetics, however, SPA-S-843 cytotoxicity on WEHI-3B (D+) cells appears substantially higher. The histograms in FIG. 2 show the IC10, the IC50 and the IC90 of the two drugs on the same cell line. The study of the differences between IC values confirms that SPA-S-843 IC10, IC50 and IC90 are significantly lower, which demonstrates that its cytotoxicity is substantially higher than that of amphotericin B.

The results of the cytotoxicity study of the two drugs on cell clonogenicity, evaluated through the agar test, were expressed as percent of the number of colonies counted in the controls (untreated cells; number of WEHI-3B (D+) colonies=212±62).

The diagrams in FIG. 3 show the dose-response curves confirming SPA-S-843 substantially higher cytotoxicity. The histograms in FIG. 4 report the IC10, IC50 and IC90 values. In this case too these values indicate that, in the WEHI-3B (D+) cells, all the IC values regarding amphotericin B are significantly higher than those regarding SPA-S-843, which substantially confirms the latter drug higher cytotoxicity on the cells under examination even in a typical clonogenicity test.

All in all, the foregoing results show that in both tests of cytotoxicity of the two drugs on murine myelomonocytic leukemia cells, these cells are more sensitive to SPA-S-843 than to amphotericin B, which latter drug is well known for its cytotoxic action against all eukaryote cells.

This finding is quite surprising in that SPA-S-843, as several other partricin derivatives, were reported in literature to be generally better tolerated by animal cells. U.S. Pat. No. 5,298,495, for instance, reports that the lytic activity on erythrocytes of partricin A derivative SPA-S-843, and of other derivatives of it, appears at very high concentrations, of the order of 18 $\mu$g/ml or more (SPA-S-843 free base: total hemolytic conc.–THC>18 $\mu$g/ml). This scarce cytotoxicity towards RBC and other mammalian cells, results in a scarce systemic toxicity in the animals; in fact, as reported in the a/m U.S. patent, the dose, lethal to 50% of the animals ($LD_{50}$) by i.v. route in mice is 58 mg/kg. A comparison can be drawn with the corresponding values of amphotericin B whose THC is 2 $\mu$g/ml and $LD_{50}$ is 4.77 mg/kg i.v. in mice (T. Bruzzese et al., Eur.J.Med.Chem., 31 , 965–72, 1996). As suggested by the foregoing comments and by FIGS. 1–4 herewith attached, SPA-S-843 toxicity occurs at sensibly lower concentrations in the case of some tumor cells such as, for instance, the WHEI-3B(D+).

The observation of this unexpected highly selective cell toxicity of some partricin derivatives on some tumor cell lines, will allow these drugs to be given, following, possibly, a suitable screening of in vitro cytotoxicity, a selective indication for the treatment of some tumors due to cells sensitive to the said derivatives. Selectivity of the antineoplastic activity will be assessed, for instance, by preliminarily performing an in vitro cytotoxicity test on tumor cells and healthy cells obtained from the same organ or tissue affected by the tumor, using a derivative of partricin A and/or B selected for the treatment of the tumor. This comparison could also be drawn using other healthy cells obtained from the same organism affected by the tumor, (for instance, an animal, preferably a mammal) which may potentially be considered sensitive to the cytotoxic effect of the partricin derivative selected for treatment.

As already mentioned, the partricin derivatives could also be used as synergistic adjuvants of other antineoplastic drugs (e.g., platinum derivatives, doxorubicin, vincristine, methotrexate etc.).

It is know, for instance, that some tumor cell lines, or some cells in particular, are, or may become, resistant to the best known antineoplastic drugs, which often leads to recurrence of the disease, and serious prejudice to the successful outcome of chemotherapy. It has also been suggested that some drugs, active on cell membrane through complexation with the sterols of cell wall, such as amphotericin B (for instance, Kuwano et al., "Techniques to reverse or circumvent drug resistance in vitro", Prog. Clin. Biol. Res. 223, 163–71, 1986; Morikage et al., "Reversal of cisplatin resistance with amphotericin B in a non-small cell lung tumor cell line", Japan J. Cancer Res., 82 , 747–51, 1991) can interact with the cells resistant to the antineoplastic drug, thus modifying their membrane permeability and accumulating the chemotherapeutic agent into the cell, thereafter restoring cell sensitivity to the drug. We have experimentally tested cisplatin (CP) chemotherapeutic activity on thyroid medullary carcinoma (TMC) cells and have confirmed, through a cytotoxicity test (MTT), that their resistance to cisplatin was substantially counteracted by pre-treatment with SPA-S-843 (2 $\mu$g/ml).

Notwithstanding this relatively low concentration, SPA-S-843 was able to potentiate cisplatin cytotoxicity against resistant cells up to the level of naturally sensitive cells; in conclusion, incubation with SPA-S-843 was able to potentiate cisplatin antineoplastic activity to such an extent as to make it cytotoxic for all TMC cells.

The above mentioned ester and amide derivatives of partricin A and/or B can be used in a method of treatment of animals, preferably mammals, in which tumoral cells are present and/or tend to develop and which are in need of antitumoral treatment.

According to said method the dosage of partricin A and/or B derivative to be administered to said animals depends on the weight and age of the animal, the severity of the desease (i.e. the amount and/or the stage of development of the tumoral cells present in the animal) and may be adjusted according to the response of the tumor affected animal to the specific partricin A and/or B derivative and the judgement of the person who controls the administration of the said partricin A and/or B derivative to said animal.

In general, the effective dosage ranges from about 0.025 to about 3 mg a day per kilogram of body weight, preferably from about 0.15 to about 1.5 mg a day per kilogram of body weight. Said dosage may be administered as a single dose or subdivided in two or more fractions. Said dosage can be given every day or at intervals (e.g. every 2 to 7 days) depending on the pathological conditions and the severity of the disease. The usual administration route is the parenteral route, with the intravenous route being preferred, in particular in the form of drip infusion to be administered in a time period of 0.5 to 8 hours. SPA-S-843 pharmaceutical formulations, intended for use as antineoplastic agents, contain 1 to 100 mg of active ingredient, preferably 5 to 50 mg, and are prepared following the usual techniques. These formulations preferably contain ascorbic acid/sodium ascorbate as an antioxidant and stabiliser and are more often preserved in the solid form, f.e., following freeze-drying. An example of a typical, but not limiting, formulation for the intravenous use is as follows:

| | |
|---|---|
| SPA-S-843 | 25 mg |
| Ascorbic acid | 4.5 mg |
| Lactose | 250 mg |
| Sterile bidistilled water q.s. to | 5 ml |

The solution is generally lyophilised, to be dissolved in 5% glucose solution (50–500 ml) before use to be administered as a slow infusion.

When the derivatives of partricin A and/or B are used as adjuvants of the antineoplastic activity of other antineoplastic drugs, the pharmaceutical formulations can contain both active ingredients in a single dosage form, or the same active ingredients can be contained in separate dosage forms permitting their composition as a single dosage form (e.g., a solution, or a suspension for administration other than intravenous administra-tion) at the time of use. Alternatively, the two active ingredients can be enclosed in separate dosage forms allowing their sequential administration during antineoplastic therapy.

I claim:

1. A method of inhibiting the growth of tumor cells sensitive to at least one compound represented by formula (I):

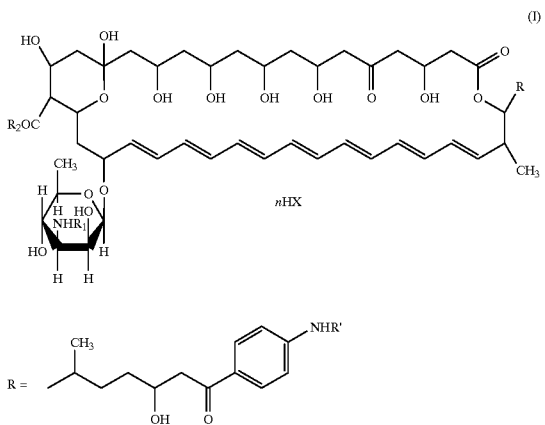

wherein

R' is a hydrogen atom or a methyl group;

$R_1$ is an aminoacyl radical —$CO(CH_2)_m NR_3 R_4$, wherein m=1, 2 or 3, $R_3$ and $R_4$, which can be the same or different, are a hydrogen atom or a $C_1$–$C_3$ alkyl group or form with the nitrogen atom to which they are bound, a five- or six-membered heterocyclic ring optionally containing another hetero atom selected from the group consisting of O, S and N, wherein said N may be substituted by a methyl or 2-hydroxyethyl group;

$R_2$ is a hydroxy, $C_1$–$C_6$ alkoxy, $NR_3R_4$ amino or —NH—$(CH_2)_m$—$NR_3R_4$ aminoalkylamino group, wherein m, $R_3$ and $R_4$ are as defined above, or a substituted —NH—$(CH_2)_m$—$R_5$ alkylamino group, wherein m is as defined above, and $R_5$ is a five- or six-membered heterocyclic ring, wherein the heteroatom is nitrogen which may be substituted with a methyl or ethyl group;

X is the anion of a pharmaceutically acceptable organic or inorganic acid; and n is 0, 1 or 2, comprising administering to an animal in need thereof an effective amount of said at least one compound represented by formula (I).

2. The method of claim 1, wherein the animal is a mammal.

3. The method of claim 1, wherein the tumor cells comprise leukemia cells, lymphoma cells, myeloma cells, melanoma cells, carcinoma cells or sarcoma cells.

4. The method of claim 1, wherein $R_1$ is selected from the group consisting of

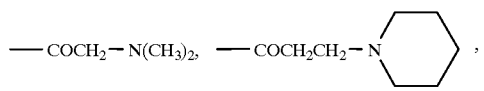

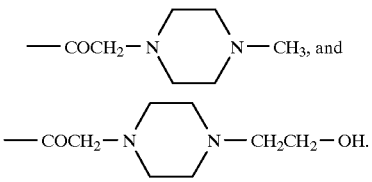

5. The method of claim 1, wherein $R_2$ is selected from the group consisting of

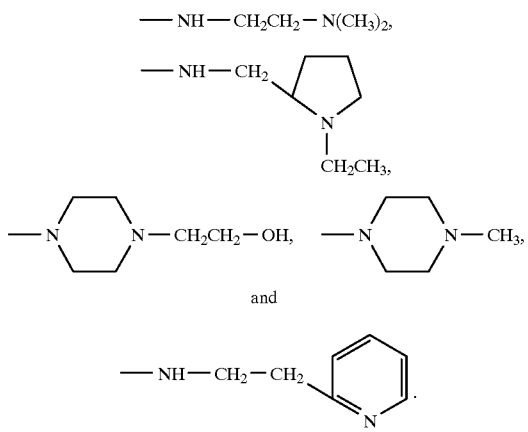

6. The method of claim 1, wherein X is the anion of an acid selected from the group consisting of aspartic, glutamic, glycolic, glucuronic, gluconic and ascorbic acid.

7. The method of claim 1, wherein the compound of formula (I) is N-dimethylaminoacetyl-partricin A 2-dimethylaminoethyl amide or a pharmaceutically acceptable salt thereof.

8. The method of claim 1, wherein the compound of formula (I) is N-dimethylaminoacetyl-partricin A 2-dimethylaminoethyl amide diascorbate.

9. The method of claim 1, wherein the compound of formula (I) is administered by a parenteral route at a dose of about 0.025 to about 3 mg a day per kilogram of body weight of the animal.

10. The method of claim 1, wherein said N-dimethylaminoacetyl-partricin A 2-dimethylaminoethyl amide or a pharmaceutically acceptable salt thereof is administered by a parenteral route at a dose of about 0.025 to about 3 mg a day per kilogram of body weight of the animal.

11. A method of inhibiting the growth of tumor cells sensitive to N-dimethylaminoacetyl-partricin A 2-dimethylaminoethyl amide or a pharmaceutically acceptable salt thereof, comprising administering to a mammal in need thereof an effective amount of said N-dimethylaminoacetyl-partricin A 2-dimethylaminoethyl amide or a pharmaceutically acceptable salt thereof.

12. The method of claim 11, wherein the tumor cells comprise leukemia cells, lymphoma cells, myeloma cells, melanoma cells, carcinoma cells or sarcoma cells.

13. The method of claim 11, wherein N-dimethylaminoacetyl-partricin A 2-dimethylaminoethyl amide diascorbate is administered to the mammal.

* * * * *